(12) United States Patent
García-Luzón et al.

(10) Patent No.: US 7,652,002 B2
(45) Date of Patent: Jan. 26, 2010

(54) 9-AMINOACYL TETRACYCLINE COMPOUNDS AND METHODS OF USE THEREOF

(75) Inventors: Carmen García-Luzón, Madrid (ES); Juan Carlos Cuevas, Madrid (ES); Jose M. Fiandor, Madrid (ES); Araceli Mallo, Madrid (ES); Mark L. Nelson, Norfolk, MA (US); Roger Frechette, Reading, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 11/643,752

(22) Filed: Dec. 20, 2006

(65) Prior Publication Data

US 2007/0270389 A1    Nov. 22, 2007

Related U.S. Application Data

(63) Continuation of application No. 10/636,437, filed on Aug. 6, 2003, now Pat. No. 7,208,482, which is a continuation of application No. 10/295,708, filed on Nov. 15, 2002, now abandoned, which is a continuation of application No. 10/097,095, filed on Mar. 12, 2002, now abandoned.

(30) Foreign Application Priority Data

Mar. 13, 2001    (EP) ................... 01500065

(51) Int. Cl.
  *A61K 31/65* (2006.01)
  *C07C 237/26* (2006.01)
(52) U.S. Cl. .......... 514/152; 552/203; 552/205
(58) Field of Classification Search ............ 514/152; 552/203, 205
  See application file for complete search history.

(56) References Cited

U.S. PATENT DOCUMENTS

| | | |
|---|---|---|
| 3,007,965 A | 11/1961 | Growich, Jr. et al. |
| 3,226,436 A | 12/1965 | James et al. |
| RE26,253 E | 8/1967 | Petisi et al. |
| 3,338,963 A | 8/1967 | James et al. |
| RE26,271 E | 9/1967 | Boothe et al. |
| 3,341,585 A | 9/1967 | Martell, Jr. et al. |
| 3,345,279 A | 10/1967 | Levy |
| 3,345,410 A | 10/1967 | Winterbottom et al. |
| 3,360,561 A | 12/1967 | Zambrano |
| 3,373,193 A | 3/1968 | Schroeder et al. |
| 3,397,230 A | 8/1968 | Winterbottom et al. |
| 3,454,697 A | 7/1969 | Joyner et al. |
| 3,483,251 A | 12/1969 | Zambrano |
| 3,518,306 A | 6/1970 | Ross et al. |
| 3,579,579 A | 5/1971 | Ross et al. |
| 4,018,889 A | 4/1977 | Armstrong |
| 4,024,272 A | 5/1977 | Rogalski et al. |
| 5,248,797 A | 9/1993 | Sum |
| 5,281,628 A | 1/1994 | Hlavka et al. |
| 5,284,963 A | 2/1994 | Sum et al. |
| 5,326,759 A | 7/1994 | Hlavka et al. |
| 5,328,902 A | 7/1994 | Sum et al. |
| 5,371,076 A | 12/1994 | Lee et al. |
| 5,380,888 A | 1/1995 | Sum et al. |
| 5,386,041 A | 1/1995 | Sum et al. |
| 5,401,729 A | 3/1995 | Sum et al. |
| 5,401,863 A | 3/1995 | Hlavka et al. |
| 5,420,272 A | 5/1995 | Sum et al. |
| 5,430,162 A | 7/1995 | Sum et al. |
| 5,442,059 A | 8/1995 | Sum et al. |
| 5,457,096 A | 10/1995 | Sum et al. |
| 5,466,684 A | 11/1995 | Sum et al. |
| 5,494,903 A | 2/1996 | Hlavka et al. |
| 5,495,018 A | 2/1996 | Sum et al. |
| 5,495,030 A | 2/1996 | Sum et al. |
| 5,495,031 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,567,692 A | 10/1996 | Sum et al. |
| 5,639,742 A | 6/1997 | Lee et al. |
| 5,675,030 A | 10/1997 | Krishnan et al. |
| 5,834,450 A | 11/1998 | Su |
| 5,886,175 A | 3/1999 | Sum et al. |
| 6,500,812 B2 | 12/2002 | Nelson et al. |

(Continued)

FOREIGN PATENT DOCUMENTS

EP    535346 B1    4/1993

(Continued)

OTHER PUBLICATIONS

Baldini, M., et al. "Diazo derivatives of amino acids and peptides as possible antineoplastic chemotherapeutic agents. 1. General considerations and methods." *Boll Soc Ital Biol Sper*. Jun. 30, 1960; 36:577-81.

(Continued)

*Primary Examiner*—Rei-tsand Shiao
(74) *Attorney, Agent, or Firm*—Ivor R. Elriffi; Heidi A. Erlacher; Mintz Levin Cohn Ferris Glovsky and Popeo PC

(57) ABSTRACT

A compound of formula (I):

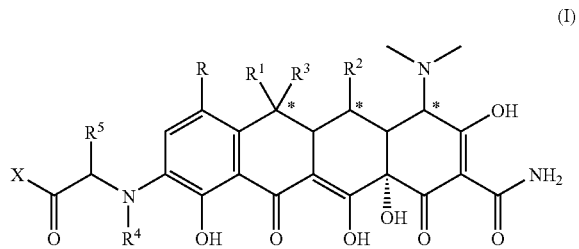

17 Claims, No Drawings

U.S. PATENT DOCUMENTS

| | | | |
|---|---|---|---|
| 6,506,740 B1 | 1/2003 | Ashley et al. | |
| 6,617,318 B1 | 9/2003 | Nelson et al. | |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,841,546 B2 * | 1/2005 | Draper et al. | 514/152 |
| 6,846,939 B2 * | 1/2005 | Nelson et al. | 552/205 |
| 7,208,482 B2 * | 4/2007 | Garcia-Luzon et al. | 514/152 |
| 2002/0103171 A1 | 8/2002 | Nelson et al. | |
| 2002/0111335 A1 | 8/2002 | Nelson et al. | |
| 2002/0115644 A1 | 8/2002 | Levy et al. | |
| 2002/0193354 A1 | 12/2002 | Nelson et al. | |
| 2003/0100017 A1 | 5/2003 | Draper et al. | |
| 2003/0125348 A1 | 7/2003 | Nelson et al. | |
| 2003/0166585 A1 | 9/2003 | Draper et al. | |
| 2005/0038002 A1 | 2/2005 | Nelson et al. | |

FOREIGN PATENT DOCUMENTS

| | | | |
|---|---|---|---|
| EP | 536515 | B1 | 4/1993 |
| EP | 0 582 788 | B1 | 2/1994 |
| EP | 0 582 789 | B1 | 2/1994 |
| EP | 0 582 829 | B1 | 2/1994 |
| EP | 582790 | B1 | 2/1994 |
| EP | 582810 | B1 | 2/1994 |
| EP | 0 618 190 | B1 | 10/1994 |
| GB | 921252 | | 3/1963 |
| GB | 955766 | | 4/1964 |
| WO | WO 01/19784 | A1 | 3/2001 |
| WO | WO 01/74761 | A1 | 10/2001 |
| WO | WO 02/04406 | A2 | 1/2002 |
| WO | WO 02/04406 | A3 | 1/2002 |
| WO | WO 02/04407 | A2 | 1/2002 |
| WO | WO 02/04407 | A3 | 1/2002 |

OTHER PUBLICATIONS

Barden, T.C., et al. ""Glycylcyclines". 3. 9-Aminodoxycyclinecarboxamides." *J Med Chem* Sep. 30, 1994; 37(20):3205-11.

Boothe, J., et al. "6-Deoxytetracyclines. I. Chemical modification by electrohilic substitution." *J. Am. Chem. Soc.* Mar. 5, 1960; 82:1253-4.

Branceni, D., et al. "Use of tetracycline for the demonstration of the phenomena of extra-osseous calcification." *C.R. Seances Soc Biol Fil.* 1961; 155:1469-72.

Dumova, A.M. "Effect of tetracycline and oxytetracycline on the adrenal function."*Antibiotiki*. Jul. 1965; 10(7):647-50.

*Federal Register*. 1962; 27:3851.

Garrod, L.P. "Recent developments in antibiotic therapy." *Recenti Prog Med*. Jan. 1962; 32:3-24.

Genazzini, E., et al. *Influenza Di Alcuni Ioni Nell'Interazione Tra Tetracicline E Sieroalbumina. Atti. Soc. Ital. Sci. Vet.* 1964; 18:175-8.

Good, W. "The inhibition of haemolysis by phloridzin." *Biochim Biophys Acta*. Jan. 29, 1969; 56:359-61.

Hajdu, P. Kurze Mitteilungen. *Arzneimittel-Forsch*. 1962; 12:206-7.

Maniar, A., et al. "One of the factors influencing the action of antibiotics." *Ann Inst Pasteur* (Paris). Dec. 1961; 101:887-97.

Martell, et al. The 6-Deoxytetracyclines. *J. Med. Chem.* 1967; 10(3);359-63.

Ritzerfeld, W., et al. "In vitro studies on 2 old and 2 new tetracycline preparations." *Arzneimittelforschung*. Jan. 1962; 12:30-2.

Strel'nokov. Effect of Tetracyclines on the Heart in Experiments by the Data of Electrocardiograms. *Antibiotiki*. 1965; 10(7):650-6.

Sum, P., et al. "Glycylcyclines. 1. A new generation of potent antibacterial agents through modification of 9-aminotetracyclines." *J Med Chem*. Jan. 7, 1994; 37(1):184-8.

Van den Bogert, C., et al. "Doxycycline in combination chemotherapy of a rat leukemia." *Cancer Res*. Dec. 1, 1988; 48(23):6686-90.

* cited by examiner

9-AMINOACYL TETRACYCLINE COMPOUNDS AND METHODS OF USE THEREOF

RELATED APPLICATIONS

This application is a continuation application of U.S. patent application Ser. No. 10/636,437, filed Aug. 6, 2003, Issuing; which is a continuation application of U.S. patent application Ser. No. 10/295,708, filed Nov. 15, 2002; which is a continuation application of U.S. patent application Ser. No. 10/097,095, filed Mar. 12, 2002; which claims priority to European Patent Application Serial No. 01500065.6, filed on Mar. 13, 2001, entitled "Medicamentos". The entire contents of each aforementioned applications are hereby incorporated herein by reference in their entirety.

FIELD OF THE INVENTION

The present invention relates to a novel class of chemical compounds and to their use in medicine. In particular, the invention concerns novel tetracycline derivatives, methods for their preparation, pharmaceutical compositions containing them and their use as antibiotic agents.

BACKGROUND OF THE INVENTION

Tetracycline derivatives are known for treating bacterial infections. However, there remains a need for tetracycline derivatives for the treatment of Gram-positive, Gram-negative and community acquired infections. Moreover, there remains a need for tetracycline derivatives effective against tetracycline resistant strains.

DETAILED DESCRIPTION OF THE INVENTION

The present invention provides compounds of formula (I):

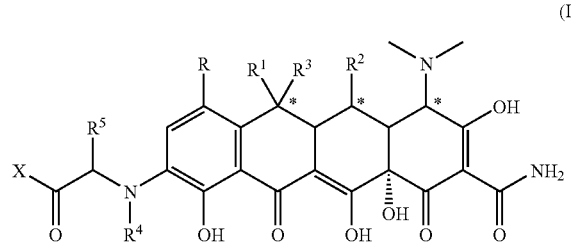

(I)

wherein:

R represents hydrogen, halogen, $C_{1-6}$alkyl or NRaRb;

$R^1$ represents hydrogen, $C_{1-6}$alkyl or together $R^1$ and $R^3$ represent a $CH_2$ moiety;

$R^2$ represents hydrogen, —$OC^{1-6}$alkyl, —$O(O)C_{1-6}$alkyl or hydroxy;

$R^3$ represents hydrogen, hydroxy or together $R^3$ and $R^1$ represent a $CH_2$ moiety;

$R^4$ represents hydrogen or $C_{1-6}$alkyl;

$R^5$ represents hydrogen, $C_{1-6}$alkyl, or $C_{1-6}$alkoxycarbonyl;

X represents NRxRy or —$OC_{1-6}$alkyl optionally substituted by one or more groups selected from hydroxy, methoxy, halogen, amino and trifluoromethyl; Ra and Rb independently represent hydrogen or $C_{1-6}$alkyl;

Rx and Ry independently represent hydrogen, benzyl, $C_{3-6}$cycloalkyl, $C_{3-6}$alkenyl, $C_{3-6}$alkynyl, $C_{1-6}$alkyl optionally substituted by one or more groups selected from hydroxy, methoxy, halogen, NRaRb and trifluoromethyl, —$C_{1-6}$alkylcycloalkyl, —$C_{1-6}$alkylheterocycle, $C_{1-6}$alkylamino and $C_{1-6}$alkylthio or together Rx and Ry form a heterocycle, and pharmaceutically acceptable derivatives and solvates thereof Compounds of formula (I) contain at least one asymmetric centre, denoted by *, and thus may exist as enantiomers or diastereoisomers. It is to be understood that the invention includes each such isomer, either in substantially pure form or admixed in any proportion with one or more other isomers of the compounds of formula (I). The preferred stereochemistry at the centre where $R^1$ and $R^3$ are substituents is when $R^1$ is H, $R^3$ is in the alpha-configuration (downwards). The preferred stereochemistry at the centre where $R^2$ is a substituent is alpha (downwards). The preferred stereochemistry at the centre where $N(Me)_2$ is a substituent in the A ring is alpha (downwards).

The term "pharmaceutically acceptable derivative" as used herein refers to any pharmaceutically acceptable salt, or metabolically labile derivative of a compound of formula (I), for example a derivative of an amine group, which, upon administration to the recipient, is capable of providing (directly or indirectly) a compound of formula (I). It will be appreciated by those skilled in the art that the compounds of formula (I) may be modified to provide pharmaceutically acceptable derivatives thereof at any of the functional groups in the compounds of formula (I). Such derivatives are clear to those skilled in the art, without undue experimentation, and with reference to the teaching of Burger's Medicinal Chemistry And Drug Discovery, 5th Edition, Vol 1: Principles And Practice, which is incorporated herein by reference. For example compounds of formula (I) may be N-alkylated in the presence of formaldehyde and an amine such as methylamine to give the corresponding Mannich base adducts.

Salts and solvates of compounds of formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and their pharmaceutically acceptable derivatives, and solvates.

Suitable salts according to the invention include those formed with both organic and inorganic acids or bases. Pharmaceutically acceptable acid addition salts include those formed from trifluoroacetic, hydrochloric, hydrobromic, hydroiodoic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic, and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Suitable solvates according to the invention include hydrates.

The term "alkyl", as used herein to define a group or a part of a group, unless otherwise stated, refers to a saturated straight or branched alkyl chain containing from 1 to 6 carbon atoms. Examples of such groups include without limitation methyl, ethyl, n-propyl, isopropyl, n-butyl, iso-butyl, sec-butyl, tert-butyl, neopentyl and hexyl.

The term "alkenyl", as used herein to define a group or a part of a group, unless otherwise stated, refers to a straight or branched alkenyl chain containing from 2 to 6 carbon.

Examples of such groups include without limitation 1-ethenyl, 1-propenyl, allyl(2-propenyl), 1-butenyl, 2-butenyl, 2-pentenyl.

The term "alkynyl", as used herein to define a group or a part of a group, unless otherwise stated, refers to a straight or branched alkynyl chain containing from 3 to 6 carbon. Examples of such groups include without limitation propynyl, butynyl or pentynyl.

The term "cycloalkyl" as used herein to define a group or a part of a group, unless otherwise stated, refers to a saturated alkyl ring containing from 3 to 6 carbon atoms. Examples of such groups include cyclopropyl, cyclobutyl, cyclopentyl and cyclohexyl.

The term "alkylamino" as used herein to define a group or a part of a group, unless otherwise stated, refers to a saturated straight or branched alkyl chain containing from 1 to 6 carbon atoms substituted by one or more amino groups. Examples of such groups include without limitation methylamino and tert-butylamino.

The term "alkylthio" as used herein to define a group or a part of a group, unless otherwise stated, refers to a saturated straight or branched alkyl chain containing from 1 to 6 carbon atoms substituted by one or more thiol groups. Examples of such groups include without limitation methylthio and tert-butylthio.

The term "halogen" refers to a fluorine, chlorine, bromine or iodine atom. Suitably the halogen atom is selected from chlorine, bromine or iodine, preferably chlorine or bromine. Chlorine is most preferred.

The term "heterocycle", as used herein refers to a 3, 4, 5 or 6 membered saturated or unsaturated heterocyclic ring containing at least one heteroatom selected from nitrogen, oxygen or sulphur. Suitable examples include without limitation tetrahydrofuran, furan, thiophene, pyridine, pyrrole, 2-pyrroline, 3-pyrroline, pyrrolidine, imidazole, 2-imidazoline, imidazolidine, pyrazole, 2-pyrazoline, pyrazoline, pyrazolidine, aziridine, 1,2,3-triazole, 1,2,4-triazole, 1,2,3-thiadiazole, piperidine, morpholine, thiomorpholine and piperazine. It will be appreciated by those skilled in the art that when X represents NRxRy and together Rx and Ry form a heterocycle, the heterocylce will contain at least one nitrogen atom. Examples of suitable nitrogen containing herterocylces include, without limitation, pyrrole, 2-pyrroline, 3-pyrroline, pyrrolidine, imidazole, 2-imidazoline, imidazolidine, pyrazole, 2-pyrazoline, pyrazoline, pyrazolidine, aziridine, 1,2,3-triazole, 1,2,4-triazole, 1,2,3-thiadiazole, piperidine, morpholine, thiomorpholine and piperazine.

Suitably, R is selected from hydrogen, methyl, chlorine and NRaRb. More suitably, R is selected from methyl, chlorine and NRaRb. Conveniently, R is selected from hydrogen, methyl, and NRaRb. More conveniently, R is selected from methyl, and NRaRb. Preferably, R is selected from hydrogen and NRaRb. More preferably, R is hydrogen.

Suitably, $R^1$ represents hydrogen, methyl or together $R^1$ and $R^3$ represent a $CH_2$ moiety. Conveniently, $R^1$ is selected from hydrogen and methyl. More conveniently, $R^1$ is hydrogen. Preferably $R^1$ is methyl.

Suitably, $R^2$ is selected from hydrogen, methoxy and hydroxy. More suitably, $R^2$ is selected from hydrogen and hydroxy. Conveniently, $R^2$ is hydroxy. Preferably, $R^2$ is hydrogen.

Suitably, $R^3$ represents hydrogen or hydroxy. Conveniently $R^3$ is hydroxy. Preferably $R^3$ is hydrogen.

Suitably, $R^4$ represents methyl or hydrogen. Conveniently $R^4$ is methyl. Preferably, $R^4$ is hydrogen.

Suitably, $R^5$ represents methyl or hydrogen. Conveniently $R^5$ is methyl. Preferably, $R^5$ is hydrogen.

Suitably, X represents NRxRy. Conveniently, X represents —$OC_{1-6}$alkyl.

Suitably, Ra and Rb independently represent hydrogen or methyl. Conveniently Ra and Rb are methyl. Preferably, Ra and Rb are hydrogen.

Suitably, Rx and Ry independently represent hydrogen, benzyl, $C_{3-6}$cycloalkyl, $C_{3-6}$alkenyl, $C_{1-6}$alkyl optionally substituted by one or more groups selected from hydroxy, methoxy, and NRaRb, —$C_{1-3}$alkylcycloalkyl, —$C_{1-3}$alkylheterocycle, $C_{1-6}$alkylamino and $C_{1-6}$alkylthio or together Rx and Ry form a heterocycle. More suitably, Rx and Ry independently represent hydrogen, benzyl, $C_{3-6}$cycloalkyl, $C_{3-6}$alkenyl, $C_{1-6}$alkyl, —$C_{1-3}$alkylcycloalkyl, —$C_{1-3}$alkylheterocycle, or together Rx and Ry form a heterocycle. Conveniently, Rx and Ry independently represent hydrogen, benzyl, $C_{3-6}$cycloalkyl, $C_{3-6}$alkenyl, $C_{1-6}$alkyl, or together Rx and Ry form a heterocycle. More conveniently, Rx and Ry independently represent hydrogen, benzyl, $C_{3-6}$cycloalkyl, $C_{3-6}$alkenyl and $C_{1-6}$alkyl. Preferably, Rx and Ry together form a heterocylcle.

When X represents —$OC_{1-6}$alkyl, X is suitably selected from iso-propoxy and ethoxy.

Suitably, NRxRy is selected from MeNH, $Me_2N$, EtNH, $Et_2N$, $CH_2CHCH_2NH$, $CH_3OCH_2CH_2NH$, $CH_3(CH_3)_2CHCH_2CH_2NH$, n-PrNH, n-$Pr_2N$, i-PrNH, i-$Pr_2N$, t-BuNH, t-$Bu_2N$, n-HexNH, n-$Hex_2N$, $(CH_3)_2NCH_2CH_2NH$, cyclopropyl-NH, aziridine, cyclobutyl-NH, cyclopentyl-NH, pyrrolidine, cyclohexylNH, propenyl-NH, benzyl-NH, piperidine, piperazine, morpholine and thiomorpholine. Preferably, NRxRy is selected from MeNH, $Me_2N$, EtNH, $CH_2CHCH_2NH$, $CH_3OCH_2CH_2NH$, n-PrNH, i-PrNH, n-HexNH, $(CH_3)_2NCH_2CH_2NH$, $CH_3(CH_3)_2CHCH_2CH_2NH$, cyclopropyl-NH, aziridine, cyclobutyl-NH, cyclopentyl-NH, pyrrolidine, cyclohexylNH, propenyl-NH, benzyl-NH, piperidine, piperazine and thiomorpholine.

Suitably the compound of formula (I) is derivatised from a natural tetracycline like compound. Examples of natural tetracycline like compounds include tetracycline, chlortetracycline, oxytetracycline, demeclocycline, methacycline, sancycline, doxycycline, and minocycline. Preferably the natural tetracycline like compound is selected from sancycline, doxycycline, and minocycline, most preferably doxycycline and sancycline.

It is to be understood that the present invention covers all combinations of suitable, convenient and preferred groups described hereinabove.

In one embodiment, R is hydrogen, $R^1$ is methyl, $R^2$ is hydroxy, $R^3$ is hydrogen, $R^4$ is hydrogen, $R^5$ is hydrogen, X represents NRxRy and Rx and Ry are independently selected from hydrogen, benzyl, $C_{3-6}$cycloalkyl, $C_{3-6}$alkenyl, $C_{1-6}$alkyl optionally substituted by one or more groups selected from hydroxy, methoxy, and NRaRb, —$C_{1-3}$alkylcycloalkyl, —$C_{1-3}$alkylheterocycle, $C_{1-6}$alkylamino and $C_{1-6}$alkylthio or together Rx and Ry form a heterocycle.

In one embodiment, R is hydrogen, $R^1$ is hydrogen, $R^2$ is hydrogen, $R^3$ is hydrogen, $R^4$ is hydrogen, $R^5$ is hydrogen, X represents NRxRy and X represents NRxRy and Rx and Ry are independently selected from hydrogen, benzyl, $C_{3-6}$cycloalkyl, $C_{3-6}$alkenyl, $C_{1-6}$ alkyl optionally substituted by one or more groups selected from hydroxy, methoxy, and NRaRb, —$C_{1-3}$alkylcycloalkyl, —$C^{1-3}$alkylheterocycle, $C_{1-6}$alkylamino and $C_{1-6}$alkylthio or together Rx and Ry form a heterocycle.

In one embodiment, R is hydrogen, $R^1$ is methyl, $R^2$ is hydroxy, $R^3$ is hydrogen, $R^4$ is hydrogen, $R^5$ is hydrogen, X represents NRxRy and NRxRy is selected from MeNH, $Me_2N$, EtNH, $CH_2CHCH_2NH$, $CH_3OCH_2CH_2NH$, n-PrNH, i-PrNH, n-HexNH, $(CH_3)_2NCH_2CH_2NH$, $CH_3(CH_3)_2$ CHCH$_2$CH$_2$NH, cyclopropyl-NH, aziridine, cyclobutyl-NH, cyclopentyl-NH, pyrrolidine, cyclohexylNH, propenyl-NH, benzyl-NH, piperidine, piperazine and thiomorpholine.

In one embodiment, R is hydrogen, $R^1$ is hydrogen, $R^2$ is hydrogen, $R^3$ is hydrogen, $R^4$ is hydrogen, $R^5$ is hydrogen, X represents NRxRy and NRxRy is selected from MeNH, Me$_2$N, EtNH, CH$_2$CHCH$_2$NH, CH$_3$OCH$_2$CH$_2$NH, n-PrNH, i-PrNH, n-HexNH, $(CH_3)_2NCH_2CH_2NH$, $CH_3(CH_3)_2$ CHCH$_2$CH$_2$NH, cyclopropyl-NH, aziridine, cyclobutyl-NH, cyclopentyl-NH, pyrrolidine, cyclohexylNH, propenyl-NH, benzyl-NH, piperidine, piperazine and thiomorpholine.

In one embodiment, R is hydrogen, $R^1$ is methyl, $R^2$ is hydroxy, $R^3$ is hydrogen, $R^4$ is hydrogen, $R^5$ is hydrogen and X represents —OC$_{1-6}$alkyl optionally substituted by one or more groups selected from hydroxy, methoxy, halogen, amino and trifluoromethyl.

In one embodiment, R is hydrogen, $R^1$ is hydrogen, $R^2$ is hydrogen, $R^3$ is hydrogen, $R^4$ is hydrogen, $R^5$ is hydrogen and X represents —OC$_{1-6}$alkyl optionally substituted by one or more groups selected from hydroxy, methoxy, halogen, amino and trifluoromethyl.

Examples of compounds of formula (I) include:

[4S-(4a,5a,12a)]-4,7-Bis(dimethylamino)-9-[(ethoxycarbonyl)methyl]amino-1,4,4a,5,5a,6,11,12a-octahydro-3,10,12,12a-tetrahydroxy-1,11-dioxo-2-naphtacenecarboxamide;

[4S-(4a,5,5a,6,12a)]-4-(Dimethylamino)-9-[1-(ethoxycarbonyl)ethyl]amino-1,4,4a,5,5a,6,11,12a-octahydro-3,5, 10,12,12a-pentahydroxy-6-methyl-1,11-dioxo-2-naphtacenecarboxamide;

[4S-(4a,5,5a,6,12a)]-4-(Dimethylamino)-9-[(ethoxycarbonyl)methyl]amino-1,4,4a,5,5a,6,11,12a-octahydro-3,5, 10,12,12a-pentahydroxy-6-methyl-1,11-dioxo-2-naphtacenecarboxamide;

[4S-(4a,5,5a,6,12a)]-4-(Dimethylamino)-9-[(N,N-dimethylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-isopropylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-(2-propenyl)aminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(1-pyrrolidinocarbonyl)methyl]amino1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(iso-propoxycarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-benzylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-ethylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-cyclohexylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(1-piperidinocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-(2-methoxyethyl)amino-carbonyl)methyl]amino-1,4,4a,5,5a,6, 11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-cyclobutylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-(2-tetrahydrofurylmethyl)-aminocarbonyl)methyl]amino-1,4,4a,5, 5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-(3,3-dimethylbutyl)aminocarbonyl)methyl]amino-1,4,4a,5,5a,6, 11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-methylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5,5a,6,12a)]-4-(Dimethylamino)-9-[(N-cyclopropylaminocarbonyl)methyl]amino-1,4,4a,5,5a,6,11,12a-octahydro-3,5,10,12,12a-pentahydroxy-6-methyl-1,11-dioxo-2-naphtacenecarboxamide;

[4S-(4a,5a,12a)]-4,7-Bis(dimethylamino)-9-[(N,N-dimethylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N,N-dimethylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-isopropylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-ethylaminocarbonyl)methyl]amino-1,4,4a,5,5a,6,11,12a-octahydro-3, 10,12,12a-tetrahydroxy-1,11-dioxo-2-naphtacenecarboxamide;

[4S-(4a,5a,12a)]-4-(Dimethylamino)-9-[(N-(2-N',N'-dimethylaminoethyl)aminocarbonyl)methyl]amino-1,4,4a,5, 5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-cyclopropylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(1-pyrrolidinoaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-cyclopentylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-(2-propenyl) aminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-methylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-benzylaminocarbonyl)methyl]amino-1,4,4a,5,5a,6,11,12a-octahydro-3,10,12,12a-tetrahydroxy-1,11-dioxo-2-naphtacenecarboxamide;

[4S-(4a,5a,12a)]-4-(Dimethylamino)-9-[(N-cyclobutylaminocarbonyl)methyl]amino-1,4,4a,5,5a,6,11,12a-octahydro-3,10,12,12a-tetrahydroxy-1,11-dioxo-2-naphtacenecarboxamide;

4S-(4aα, 5α, 5aα, 6α, 12aα)-4,7-(bis-dimethylamino)-9-[1-(ethoxycarbonyl)ethyl]amino-1,4,4a,5,5a,6,11,12a-octahydro-3,10,12,12a-tetrahydroxy-1,11-dioxo-2-naphthacenecarboxamide;

[4S-(4aα, 5α, 5aα, 6α, 12aα)-4-(dimethylamino)-9-[(ethoxycarbonyl)-2-propyl-methyl]amino-1,4,4a,5,5a,6,11,12a-octahydro-3,5,10,12,12a-pentahydroxy -1,11-dioxo-6-methyl-2-naphthacenecarboxamide;

[4S-(4aα, 5α, 5aα, 6α, 12aα)-4-(dimethylamino)-9-[(ethoxycarbonyl)-2-carbonylethoxy methyl]amino-1,4,4a,5,5a,6,11,12a-octahydro-3,5,10,12,12a-pentahydroxy-1,11-dioxo-6-methyl-2-naphthacenecarboxamide.

References herein after to compounds of the invention include compounds of formula (I) and their pharmaceutically acceptable derivatives and solvates.

As demonstrated in the assays described below the compounds of the present invention show activity against the most important pathogens, including gram positive bacteria such as *S. pneumoniae* and *S. aureus*, and gram negative organisms such as *H. influenzae*, *M catarrhalis* and *E. coli*. In addition, these compounds are active against gram positive and gram negative tetracycline resistant bacterial strains, including those with resistance mediated by efflux pumps and ribosome protection.

Accordingly, in a further aspect the present invention provides a method for the treatment of a tetracycline compound responsive state in a subject, preferably a human, which comprises administering to the subject an effective amount of a compound of formula (I) or pharmaceutically acceptable derivative or solvate thereof.

In the alternative, there is provided a compound of formula (I) or a pharmaceutically acceptable derivative or solvate thereof, for use in medical therapy, particularly, for use in the manufacture of a medicament for the treatment of a tetracycline compound responsive state.

The term "tetracycline compound responsive state" includes a state which can be treated, prevented, or otherwise ameliorated by the administration of a compound of formula (I) or pharmaceutically acceptable derivative or solvate thereof Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important human and veterinary diseases such as respiratory tract infections, systemic infections and some local infections. More particularly, compounds of the invention can be used to prevent or control diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). In one embodiment, the tetracycline compound is used to treat a bacterial infection. In a further embodiment, the tetracycline compound is used to treat a bacterial infection that is resistant to other tetracycline antibiotic compounds.

For the avoidance of doubt, the term 'treatment' as used herein includes prophylactic therapy.

Bacterial infections may be caused by a wide variety of gram positive and gram negative bacteria. The compounds of formula (I) are useful as antibiotics against organisms which are resistant to other tetracycline compounds. The antibiotic activity of the compounds of formula (I) may be determined using the method discussed in the Biological Example below, or by using the in vitro standard broth dilution method described in Waitz, J. A., *National Committee for Clinical Laboratory Standards*, Approved Standard M7-T2, vol. 10, no. 8, pp. 13-20, $2^{nd}$ edition, Villanova, Pa. (1990).

The compounds of the invention may also be used to treat infections traditionally treated with tetracycline compounds such as, for example, rickettsiae; a number of gram-positive and gram-negative bacteria; and the agents responsible for lymphogranuloma venereum, inclusion conjunctivitis and psittacosis. The compounds of formula (I) may be used to treat infections of *pneumococci, Salmonella, E. coli, S. aureus* or *E. faecalis*.

The term "effective amount" of the compound of formula (I) is that amount necessary or sufficient to treat or prevent a tetracycline compound responsive state. The effective amount can vary depending on such factors as the size and weight of the subject, the type of illness, or the particular tetracycline compound. One of ordinary skill in the art would be able to study the aforementioned factors and make the determination regarding the effective amount of the compound of formula (I) or a pharmaceutically acceptable derivative or solvate thereof without undue experimentation.

The invention also pertains to methods of treatment against micro-organism infections and associated diseases. The methods include administration of an effective amount of one or more compounds of formula (I) or a pharmaceutically acceptable derivative or solvate thereof to a subject. Preferably the subject is a mammal e.g., a human.

For human use, a compound of the formula (I) can be administered as raw drug substance, but will generally be administered in admixture with a pharmaceutically acceptable carrier selected with regard to the intended route of administration and standard pharmaceutical practice.

Accordingly, the present invention further provides a pharmaceutical formulation comprising a compound of formula (I) or a pharmaceutically acceptable derivative or solvate thereof, and one or more pharmaceutically acceptable carriers.

The term pharmaceutically acceptable carrier includes substances capable of being coadministered with the compounds of formula (I), and which allow performance of the intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the compounds of the invention.

The compounds of the invention may be administered alone or in combination with pharmaceutically acceptable carriers or diluents. The compounds of the invention may be administered via oral, parenteral or topical routes. The administration may be carried out in single or multiple doses. The compounds of the invention may be administered in a wide variety of different dosage forms, for example they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions may be sweetened and/or flavored. In general, the compounds of the invention are present in such dosage forms at concentration levels ranging from about 5.0% to about 70% by weight.

For oral administration, tablets may contain various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulphate and talc may be employed. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents, together with diluents such as water, ethanol, propylene glycol, glycerin and various combinations thereof.

For parenteral administration (including intraperitoneal, subcutaneous, intravenous, intradermal or intramuscular injection), solutions of compounds of the invention in either sesame or peanut oil or in aqueous propylene glycol may be employed. The aqueous solutions may be buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral administration, examples of suitable preparations include solutions, preferably oily or aqueous solutions as well as suspensions, emulsions, or implants, including suppositories. Compounds of the invention may be formulated in sterile form in multiple or single dose formats. For example the compounds of the invention may be dispersed in a fluid carrier such as sterile saline or 5% saline dextrose solutions commonly used with injectables.

The compounds of the invention may be administered topically for example when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petroleum, isopropylpalmitate, polyethylene glycol, ethanol 95%, polyoxyethylene monolauriate 5% in water, sodium lauryl sulphate 5% in water, and the like. In addition, materials such as anti-oxidants, humectants, viscosity stabilisers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats.

It will be appreciated that the actual amount of the compound of the invention used in a given therapy will vary according to the specific compound being utilized, the particular compositions formulated, the mode of application, the particular site of administration, etc. Optimal administration rates for a given protocol of administration can be readily ascertained by those skilled in the art without undue burden.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

The compounds and pharmaceutical compositions of the invention may be administered alone or in combination with other known compounds and compositions for treating tetracycline compound responsive states in a mammal e.g. a human. The term in combination with a known compound or composition is intended to include simultaneous, concomitant and sequential administration.

Accordingly, the present invention provides a combination comprising a compound of formula (I) or a pharmaceutically acceptable derivative or solvate thereof, and a further active ingredient suitable for treating tetracycline compound responsive states in a mammal e.g. a human.

Compounds of Formula (I) and pharmaceutically acceptable derivatives and solvates thereof may be prepared by general methods outlined hereinafter where the groups R, $R^1$ , $R^2$, $R^3$, $R^4$, $R^5$, X, Ra, Rb, Rx and Ry have the meaning defined for compounds of formula (I) unless otherwise stated.

According to a further aspect of the invention, there is provided a process (A) for preparing a compound of Formula (I) wherein $R^5$ is hydrogen and X is NRxRy or a pharmaceutically acceptable derivative or solvate thereof which process comprises reacting a compound of formula (II) with a compound of formula (III) under dehydrating conditions for example in the presence of acetic acid, methanol and water and then subjecting the product to a reducing agent such as sodium cyanoborohydride.

(II)

(III)

According to a further aspect of the invention, there is provided a process (B) for preparing a compound of Formula (I) wherein $R^5$ is hydrogen and X is —$OC_{1-6}$ alkyl or a pharmaceutically acceptable derivative or solvate thereof which process comprises reacting a compound of formula (II) with a compound of formula (IV) under dehydrating conditions for example in the presence of acetic acid, methanol and water, subjecting the adduct to a reducing agent such as sodium cyanoborohydride and then reacting the N-glycyl derivative with the appropriate alcohol ($HOC_{1-6}$alkyl) in the presence of a catalyst such as thionyl chloride.

(IV)

According to a further aspect of the invention, there is provided a process (C) for the preparation of a compound of Formula (I) wherein $R^5$ is $C_{1-6}$alkyl or $C_{1-6}$alkoxycarbonyl and X is an $C_{1-6}$alkoxy group, an alkylamino group (e.g., $NR^xR^y$) or a carboxylic acid derivative, or a pharmaceutically acceptable derivative or solvate thereof. The process comprises reacting a compound of Formula (II) with a compound of formula (V) under conditions such that the compound is formed.

(V)

Compounds of formula (III) may be prepared by reacting compounds of formula (VI) with sodium periodate in wet dichloromethane.

(VI)

Alternatively, compounds of formula (III) may be prepared by reacting compounds of formula (VII) with an appropriate amine of formula HNRxRy and then reacting the adduct with sodium periodate in wet dichloromethane.

(VII)

SYNTHETIC EXAMPLES 9-amino tetracycline derivatives were prepared according to the following general procedures:

R, $R^1$, $R^3$, $R^2$=H (sancycline) (a) NBS/conc. $H_2SO_4$, 0° C.; (b) 10% $HNO_3$/conc. $H_2SO_4$; (c) $H_2$, Pd/C, MeOH, HCl. Ref: J. Boothe, J. J. Hlavka, J. P. Petisi, J. L. Spencer, J. Am. Chem. Soc., 1960, 82, 1253-4.

R=$NMe_2$, $R^1$, $R^3$, $R^2$=H (minocycline) (a) $HNO_3$/conc. $H_2SO_4$; (b) $H_2$, Pd/C, MeOH/HCl. Ref: P. Sum, V. L. Lee, R. T. Testa, J. J. Hlavka, G. A. Ellestad, J. D. Bloom, Y. Gluzman, F. P. Tally, J. Med. Chem, 1994, 37, 184-8.

R=H, R¹=H, R³(alpha)=Me, R²(alpha)=OH (doxycycline) (a) NaNO₃/conc. H₂SO₄; (b) H₂, Pd/C, MeOH. Ref: T. C. Barden, B. L. Buckwalter, R. T. Testa, P. J. Petersen, V. L. Lee, J. Med. Chem. 1994, 37, 3205-11.

General Procedure (A)

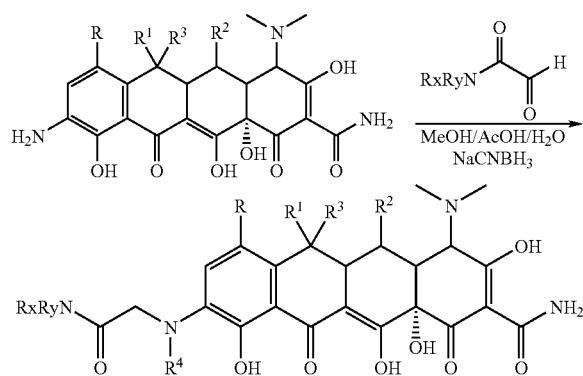

A solution of the 9-amino derivative (0.17 mmol) in a mixture of methanol (14 ml), acetic acid (0.7 ml) and water (0.7 ml) is treated with the corresponding aldehyde (0.20 mmol). After stirring at room temperature for 5 min, solid sodium cyanoborohydride (0.20 mmol) is added and the reaction solution is stirred for 1 hour. A suspension of the reaction product is then obtained either by dropwise addition of cool ether into the reaction solution (in the case of minocycline derivatives) or to the dry material after evaporating the solvent (in the case of sancy and doxycycline derivatives). Filtration of this suspension through a glass-sintered funnel affords a crude material which is purified by semi-preparative hplc (water/acetonitrile gradient). Water (0.1% trifluoroacetic acid)/acetonitrile (0.1% trifluoroacetic acid), gradient 15 to 50% acetonitrile for 45 min; Luna column (10 microns, C-8, 250×21,20 mm); compounds were detected by using UV light of a 280 nm wavelength.

General Procedure (B)

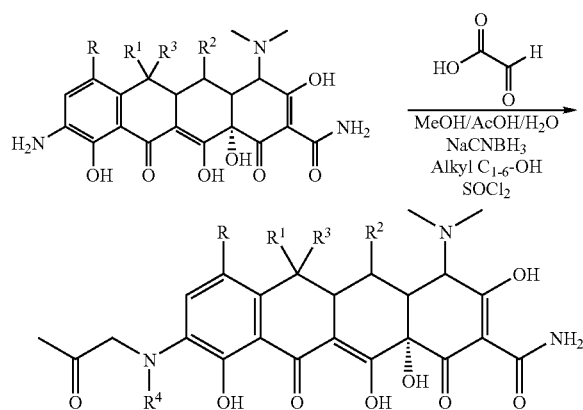

A solution of the 9-amino derivative (0.17 mmol) in a mixture of methanol (14 ml), acetic acid (0.7 ml) and water (0.7 ml) is treated with the corresponding aldehyde (0.20 mmol) to afford the 9-(N-glycyl) which is treated with thionyl chloride (10 ul) and the appropriate alcohol. The solution is stirred at room temperature for 20 h. Evaporation of the resulting reaction solution gives rise to a residue which is treated with ether. The resulting suspension is filtered through a glass-sintered funnel to afford a crude material which is purified by semi-preparative hplc (water/acetonitrile gradient). Water (0.1% trifluoroacetic acid)/acetonitrile (0.1% trifluoroacetic acid), gradient 15 to 50% acetonitrile for 45 min; Luna column (10 microns, C-8, 250×21,20 mm); compounds were detected by using UV light of a 280 nm wavelength.

General Procedure (C)

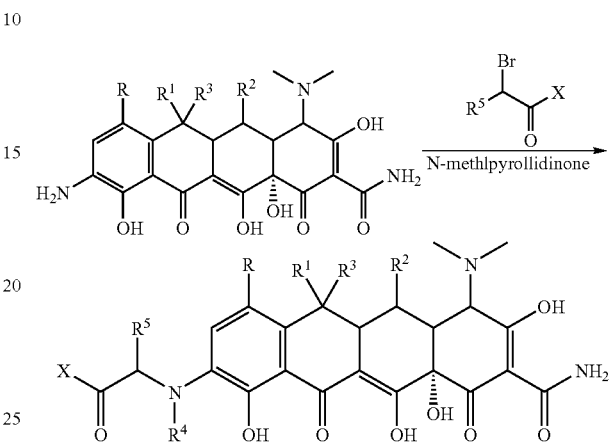

A 9-amnino derivative (0.10 mmol) is dissolved in N-methylpyrrolidinone (1.0 mL) and treated with excess (0.40 mmol) of the corresponding bromocarbonyl compound. After stirring for 4 hours at 60-65° C., the reaction mixture is cooled and is dripped slowly into cold ether producing the crude product. The solid can then be collected by filtration, and purified by preparative chromatography (phosphate buffer 0.1 M+0.001 M Na₂EDTA and methanol gradient, 30% to 100% over 30 minutes), C18 solid-phase, UV detection at 280 nm). The product fractions can then be isolated, extracted into butanol (3×10 ml), dried over Na₂SO₄, and the solvent can be removed in vacuo to yield the product.

The following compounds were prepared according to the above described general methods:

Example 1

[4S-(4a,5a,12a)]-4,7-Bis(dimethylamino)-9-[(ethoxycarbonyl)methyl]amino-1,4,4a,5,5a,6,11,12a-octahydro-3,10,12,12a-tetrahydroxy-1,11-dioxo-2-naphtacenecarboxamide MS (e.s.+): m/z 559.30 (M⁺+H)

Example 2

[4S-(4a,5,5a,6,12a)]-4-(Dimethylamino)-9-[1-(ethoxycarbonyl)ethyl]amino-1,4,4a,5,5a,6,11,12a-octahydro-3,5,10,12,12a-pentahydroxy-6-methyl-1,11-dioxo-2-naphtacenecarboxamide MS (e.s.+): m/z 560.2 (M⁺+H)

Example 3

[4S-(4a,5,5a,6,12a)]-4-(Dimethylamino)-9-[(ethoxycarbonyl)methyl]amino-1,4,4a,5,5a,6,11,12a-octahydro-3,5,10,12,12a-pentahydroxy-6-methyl-1,11-dioxo-2-naphtacenecarboxamide MS (e.s.+): m/z 546.10 (M⁺+H)

Example 4

[4S-(4a,5,5a,6,12a)]-4-(Dimethylamino)-9-[(N,N-dimethylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 545.22 (M++H)

[4S-(4a,5,5a,6,12a)]-4-(Dimethylamino)-9-[(N-isopropylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 559.24 (M++H)

[4S-(4a,5,5a,6,12a)]-4-(Dimethylamino)-9-[(N-(2-propenyl)aminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 557.19 (M++H)

[4S-(4a,5,5a,6,12a)]-4-(Dimethylamino)-9-[(1-pyrrolidinocarbonyl)methyl]amino 1,4,4a,5,5a,6,11,12a-octahydro-3,5,10,12,12a-pentahydroxy-6-methyl-1,11-dioxo-2-naphtacenecarboxamide
MS (e.s.+): m/z 571.13 (M++H)

[4S-(4a,5,5a,6,12a)]-4-(Dimethylamino)-9-[(iso-propoxycarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 560.20 (M++H)

[4S-(4a,5,5a,6,12a)]-4-(Dimethylamino)-9-[(N-benzylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 607.20 (M++H)

[4S-(4a,5,5a,6,12a)]-4-(Dimethylamino)-9-[(N-ethylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 545.2 (M++H)

[4S-(4a,5,5a,6,12a)]-4-(Dimethylamino)-9-[(N-cyclohexylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 599.3 (M++H)

[4S-(4a,5,5a,6,12a)]-4-(Dimethylamino)-9-[(1-piperidinocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 585.2 (M++H)

[4S-(4a,5,5a,6,12a)]-4-(Dimethylamino)-9-[(N-(2-methoxyethyl)amino-carbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 575.2 (M++H)

[4S-(4a,5,5a,6,12a)]-4-(Dimethylamino)-9-[(N-cyclobutylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 571.3 (M++H)

[4S-(4a,5,5a,6,12a)]-4-(Dimethylamino)-9-[(N-(2-tetrahydrofurylmethyl)-aminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 601.3 (M++H)

[4S-(4a,5,5a,6,12a)]-4-(Dimethylamino)-9-[(N-(3,3-dimethylbutyl)aminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 601.3 (M++H)

[4S-(4a,5,5a,6,12a)]-4-(Dimethylamino)-9-[(N-methylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 531.2 (M++H)

[4S-(4a,5,5a,6,12a)]-4-(Dimethylamino)-9-[(N-cyclopropylaminocarbonyl)methyl]amino-1,4,4a,5,5a,6,11,12a-octahydro-3,5,10,12,12a-pentahydroxy-6-methyl-1,11-dioxo-2-naphtacenecarboxamide
MS (e.s.+): m/z 557.2 (M++H)

[4S-(4a,5a,12a)]-4,7-Bis(dimethylamino)-9-[(N,N-dimethylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 558.19 (M++H)

[4S-(4a,5a,12a)]-4-(Dimethylamino)-9-[(N,N-dimethylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 515.09 (M++H)

[4S-(4a,5a,12a)]-4-(Dimethylamino)-9-[(N-isopropylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 529.09 (M++H)

[4S-(4a,5a,12a)]-4-(Dimethylamino)-9-[(N-ethylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 515.2 (M++H)

[4S-(4a,5a,12a)]-4-(Dimethylamino)-9-[(N-(2-N',N'-dimethylaminoethyl)aminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 558.3 (M++H)

[4S-(4a,5a,12a)]-4-(Dimethylamino)-9-[(N-cyclopropylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 527.2 (M++H)

[4S-(4a,5a,12a)]-4-(Dimethylamino)-9-[(1-pyrrolidinoaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 541.2 (M++H)

[4S-(4a,5a,12a)]-4-(Dimethylamino)-9-[(N-cyclopentylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 555.3 (M++H)

[4S-(4a,5a,12a)]-4-(Dimethylamino)-9-[(N-(2-propenyl)aminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 527.2 (M++H)

[4S-(4a,5a,12a)]-4-(Dimethylamino)-9-[(N-methylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 501.2 (M++H)

[4S-(4a,5a,12a)]-4-(Dimethylamino)-9-[(N-benzylaminocarbonyl)methyl]amino-1,4,4a,5,5a,6,11,12a-octahydro-3,10,12,12a-tetrahydroxy-1,11-dioxo-2-naphtacenecarboxamide
MS (e.s.+): m/z 577.2 (M++H)

[4S-(4a,5a,12a)]-4-(Dimethylamino)-9-[(N-cyclobutylami-nocarbonyl)methyl]amino-1,4,4a,5,5a,6,11,12a-octahydro-3,10,12,12a-tetrahydroxy-1,11-dioxo-2-naphtacen-ecarboxamide MS (e.s.+): m/z 541.2 (M$^+$+H)

[4S-(4aα, 5α, 5aα, 6α, 12aα)-4,7-(bis-dimethylamino)-9-[1-(ethoxycarbonyl)ethyl]amino-4,4a,5,5a,6,11,12a-octahydro-3,10,12,12a-tetrahydroxy-1,11-dioxo-2-naphthacen-ecarboxamide MS (e.s.)+: m/z 573.3 (M$^+$+H)

[4S-(4aα, 5α, 5aα, 6α, 12aα)-4-(dimethylamino)-9-[(ethoxycarbonyl)-2-propyl-methyl]amino-1,4,4a,5,5a,6,11,12a-octahydro-3,5,10,12,12a-pentahydroxy-1,11-dioxo-6-methyl-2-naphthacenecarboxamide MS (e.s.)+: m/z 588.3 (M$^+$+H)

[4S-(4aα, 5α, 5aα, 6α, 12aα)-4-(dimethylamino)-9-[(ethoxycarbonyl)-2-carbonylethoxy methyl]amino-1,4,4a,5,5a,6,11,12a-octahydro-3,5,10,12,12a-pentahydroxy-1,11-dioxo-6-methyl-2-naphthacenecarboxamide MS (e.s.)+: m/z 618.2 (M$^+$+H)

Biological Examples

| Organism | 1 MIC (μg/ml) | 2 MIC (μg/ml) | 3 MIC (μg/ml) | 4 MIC (μg/ml) |
|---|---|---|---|---|
| S. aureus RN4250 | 16 | 2 | 2 | — |
| S. aureus RN450 | 16 | 0.25 | 0.5 | — |
| S. aureus ATCC29213 | 16 | — | — | 0.5 |
| S. aureus ATCC 13709 | — | 0.5 | 1 | — |
| E. hirae ATCC 9790 | 8 | 0.25 | 1 | — |
| S. pneumoniae ATCC 49619 | 32 | 0.5 | 0.5 | 0.06 |
| S. pneumoniae 157E | — | 1 | — | — |
| H. influenzae ATCC 49247 | 32 | 32 | 8 | 2 |
| M. catarrhalis ATCC 23246 | 4 | 1 | 2 | — |
| E. coli 1850E | 32 | 64 | 32 | — |
| E. coli ATCC 25933 | — | — | — | 2 |

Growth-inhibitory activity was determined on liquid medium by the antibiotic dilution technique using 96-well microtiter system plates containing two-fold dilutions of antibiotic-agent in 0.2 ml. of Mueller-Hinton broth. Plates were inoculated with each test organism to yield a final inoculum of 5×10$^5$ CFU/ml and were incubated aerobically at 37° C. for 18 h. The MIC was defined as the lowest concentration of antibacterial agent that inhibited development of visible growth in the microdilution wells.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A compound of formula (I):

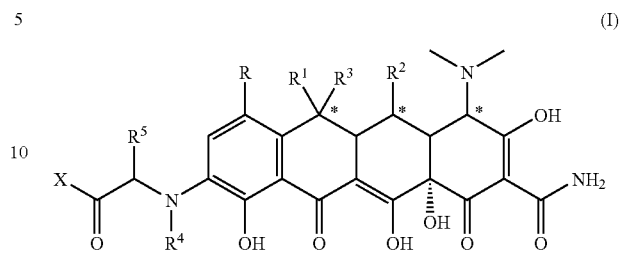

wherein:

R represents hydrogen, halogen or $C_{1-6}$alkyl;

R$^1$ represents hydrogen, $C_1$alkyl or together R$^1$ and R$^3$ represent a CH$_2$ moiety;

R$^2$ represents hydrogen, —OC$_{1-6}$alkyl, —O(O)C$_{1-6}$alkyl or hydroxy;

R$^3$ represents hydrogen, hydroxy or together R$^3$ and R$^1$ represent a CH$_2$ moiety;

R$^4$ represents hydrogen or C$_{1-6}$alkyl;

R$^5$ represents hydrogen, C$_{1-6}$alkyl or C$_{1-6}$alkoxycarbonyl;

X represents NRxRy;

Rx and Ry represent —C$_{1-6}$alkylheterocycle or together Rx and Ry form a heterocycle; and pharmaceutically acceptable salts thereof.

2. A method for the treatment of a bacterial infection in a subject, which comprises administering to the subject an effective amount of a compound of formula (I):

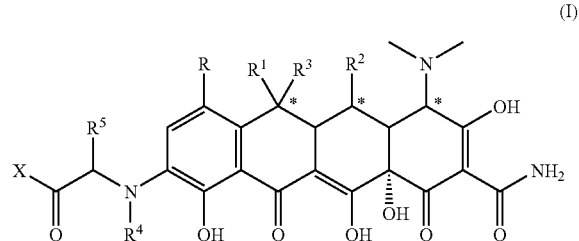

wherein:

R represents hydrogen) halogen, or C$_{1-6}$alkyl;

R$^1$ represents hydrogen, C$_{1-6}$alkyl or together R$^1$ and R$^3$ represent a CH$_2$ moiety;

R$^2$ represents hydrogen, —OC$_{1-6}$alkyl, —O(O)C$_{1-6}$alkyl or hydroxy;

R$^3$ represents hydrogen, hydroxy or together R$^3$ and R$^1$ represent a CH$_2$ moiety;

R$^4$ represents hydrogen or C$_{1-6}$alkyl;

R$^5$ represents hydrogen, C$_{1-6}$alkyl or C$_{1-6}$alkoxycarbonyl;

X represents NRxRy;

Rx and Ry represent —C$_{1-6}$alkylheterocycle or together Rx and Ry form a heterocycle; and pharmaceutically acceptable salts thereof.

3. The method of claim 2, wherein said subject is a human.

4. A pharmaceutical formulation comprising a compound of formula (I):

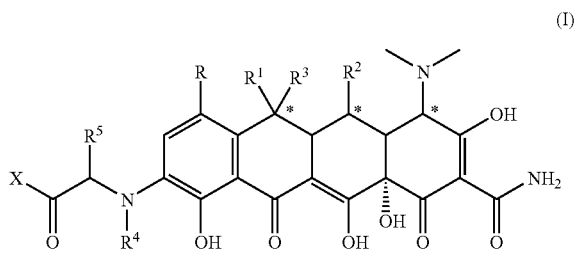

(I)

wherein:
- R represents hydrogen) halogen, or $C_{1-6}$alkyl;
- $R^1$ represents hydrogen, $C_{1-6}$alkyl or together $R^1$ and $R^3$ represent a $CH_2$ moiety;
- $R^2$ represents hydrogen, —$OC_{1-6}$alkyl, —$O(O)C_{1-6}$alkyl or hydroxy;
- $R^3$ represents hydrogen, hydroxy or together $R^3$ and $R^1$ represent a $CH_2$ moiety;
- $R^4$ represents hydrogen or $C_{1-6}$alkyl;
- $R^5$ represents hydrogen, $C_{1-6}$alkyl or $C_{1-6}$alkoxycarbonyl;
- X represents NRxRy;
- Rx and Ry represent —$C_{1-6}$alkylheterocycle or together Rx end Ry form a heterocycle; and pharmaceutically acceptable salts thereof; and one or more pharmaceutically acceptable carriers.

5. The compound of claim 1, wherein said compound is [4S-(4a,5,5a,6,12a)]-4-(Dimethylamino)-9-[(-pyrrolidinocarbonyl)methyl]amino -1,4,4a,5,5a,6,11,12a-octahydro-3,5,10,12,12a-pentahydroxy-6-methyl-1,11-dioxo-2-naphthacenecarboxamide.

6. The compound of claim 1, wherein said compound is [4S-(4a,5,5a,6,12a)]-4-(Dimethylamino)-9-[(1-piperidinocarbonyl)methyl]amino -1,4,4a5,5a,6,11,12a-octahydro-3,5,10,12,12a-pentahydroxy-6-methyl -1,11-dioxo-2-naphthacenecarboxamide.

7. The compound of claim 1, wherein said compound is [4S-(4a,5a,12a)]-4-(Dimethylamino)-9-[(1-pyrrolidinoaminocarbonyl)methyl]amino -1,4,4a,5,5a,6,11,12a-octahydro-3,10,12,12a-tetrahydroxy-1,11-dioxo-2-naphthacenecarboxamide.

8. The method of claim 2, wherein said compound is [4S-(4a,5,5a,6,12a)]-4-(Dimethylamino)-9-[(1-pyrrolidinocarbonyl)methyl]amino -1,4,4a,5,5a,6,11,12a-octahydro-3,5,10,12,12a-pentahydroxy-6-methyl-1,11-dioxo-2-naphthacenecarboxamide.

9. The method of claim 2, wherein said compound is [4S-(4a,5,5a,6,11,12a)]-4-(Dimethylamino)-9-[(1-piperidinocarbonyl)methyl]amino -1,4,4a,5,5a,6,11,12a-octahydro-3,5,10,12,12a-pentahydroxy-6-methyl-1,11-dioxo-2-naphthacenecarboxamide.

10. The method of claim 2, wherein said compound is [4S-(4a,5a,12a)]-4-(Dimethylamino)-9-[(1-pyrrolidinoaminocarbonyl)methyl]amino -1,4,4a,5,5a,6,11,12a-octahydro-3,10,12,12a-tetrahydroxy-1,11-dioxo-2-naphthacenecarboxamide.

11. The pharmaceutical formulation of claim 4, wherein said compound is [4S-(4a,5,5a,6,12a)]-4-(Dimethylamino)-9-[(1-pyrrolidinocarbonyl)methyl]amino-1,4,4a,5,5a,6,11,12a-octahydro-3,5,10,12,12a -pentahydroxy-6-methyl-1,11-dioxo-2-naphthacenecarboxamide.

12. The pharmaceutical formulation of claim 4, wherein said compound is [4S-(4a,5,5a,6,12a)]-4-(Dimethylamino)-9-[(1-piperidinocarbonyl)methyl]amino1,4,4a,5,5a,6,11,12a-octahydro-3,5, 10,12,12a -pentahydroxy-6-methyl-1,11-dioxo-2-naphthacenecarboxamide.

13. The pharmaceutical formulation of claim 6, wherein said compound is [4S-(4a,5a,12a)]-4-(Dimethylamino)-9-[(1-pyrrolidinoaminocarbonyl)methyl]amino-1,4,4a,5,5a,6,11,12a-octahydro-3,10,12,12a -tetrahydroxy-1,11-dioxo-2-naphthacenecarboxamide.

14. The method of claim 2, wherein said bacterial infection is a gram positive bacterium.

15. The method of claim 2, wherein said bacterial infection is a gram negative bacterium.

16. The method of claim 2, wherein said bacterial infection is *S. pneumoniae* or *S. aureus*.

17. The method of claim 2, wherein said bacterial infection is *H. influenzae, M catarrhalis* or *E coli*.

\* \* \* \* \*